United States Patent
Nishino et al.

(10) Patent No.: US 8,945,299 B2
(45) Date of Patent: Feb. 3, 2015

(54) METHOD FOR PURIFYING ETHYL-2-CYANOACRYLATE ADHESIVE COMPOSITION AND ETHYL-2-CYANOACRYLATE ADHESIVE COMPOSITION

(75) Inventors: Yukinori Nishino, Osaka (JP); Hiroaki Yamamoto, Hyogo (JP); Chiaki Hata, Osaka (JP)

(73) Assignee: Taoka Chemical Co., Ltd., Osaka (JP)

( * ) Notice: Subject to any disclaimer, the term of this patent is extended or adjusted under 35 U.S.C. 154(b) by 227 days.

(21) Appl. No.: 13/517,332

(22) PCT Filed: Nov. 30, 2010

(86) PCT No.: PCT/JP2010/071385
§ 371 (c)(1),
(2), (4) Date: Jun. 20, 2012

(87) PCT Pub. No.: WO2011/077906
PCT Pub. Date: Jun. 30, 2011

(65) Prior Publication Data
US 2012/0255461 A1    Oct. 11, 2012

(30) Foreign Application Priority Data
Dec. 25, 2009   (JP) ................................. 2009-295368

(51) Int. Cl.
*C09J 4/04*     (2006.01)
*C07C 255/08*   (2006.01)
*C09D 4/00*     (2006.01)
*C08F 220/42*   (2006.01)

(52) U.S. Cl.
CPC ............... *C07C 255/08* (2013.01); *C09D 4/00* (2013.01); *C08F 220/42* (2013.01)
USPC .................................................... 106/287.25

(58) Field of Classification Search
None
See application file for complete search history.

(56) References Cited

U.S. PATENT DOCUMENTS

| | | | |
|---|---|---|---|
| 4,444,933 A * | 4/1984 | Columbus et al. ............ | 524/292 |
| 6,057,472 A | 5/2000 | Sailhan et al. | |
| 2007/0027335 A1 | 2/2007 | Kanou et al. | |
| 2008/0075862 A1 * | 3/2008 | Melancon et al. ............ | 427/340 |

FOREIGN PATENT DOCUMENTS

| | | | |
|---|---|---|---|
| CN | 1047077 A | | 11/1990 |
| EP | 0 895 987 A1 | | 2/1999 |
| JP | 54-152033 A | | 11/1979 |
| JP | 55-151074 A | | 11/1980 |
| JP | 08-505383 A | | 6/1996 |
| JP | 11-100361 A | | 4/1999 |
| JP | 2006077183 A | * | 3/2006 |
| JP | 2007-126632 A | | 5/2007 |
| WO | 94/15907 A | | 7/1994 |

OTHER PUBLICATIONS

International Search Report for corresponding International Application No. PCT/JP2010/071385 mailed Dec. 28, 2010.
Form PCT/ISA/237 for corresponding International Application No. PCT/JP2010/071385 dated Dec. 28, 2010.
Japanese Office Action (Notification of Reasons for Refusal) for corresponding Japanese Application No. 2009-295368 issued Mar. 16, 2010.
Chinese Office Action for corresponding Chinese Application No. 201080058262.3 mailed Mar. 11, 2013 and English translation.
Yu, "Study on Synthesis Technique and Modification of α-Cyanoacrylate", Liaoning Chemical Industry, vol. 36, No. 4, Apr. 2007 and English Abstract.
Lazaris et al., "Gas Chromatographic Determination of Impurities in Ethyl Cyanoacrylate", Journal of Analytical Chemistry of the USSR, Apr. 1984, vol. 39, No. 4, Part 2, pp. 584-587.

* cited by examiner

*Primary Examiner* — Melissa Swain
(74) *Attorney, Agent, or Firm* — Renner, Otto, Boisselle & Sklar, LLP

(57) ABSTRACT

The present invention provides an ethyl-2-cyanoacrylate adhesive composition obtained as a result of significant improvement on conventional problems, that is, irritating odor and whitening of conventional ethyl-2-cyanoacrylate adhesive compositions. According to a method of the present invention for purifying an ethyl-2-cyanoacrylate adhesive composition, a sum total of an acrylonitrile content and an ethanol content is arranged to be in a range of 1 ppm to 150 ppm, by carrying out deaeration at the same time as injection of an inactive gas at a reduced pressure in a range of 100 Pa to 10000 Pa at a temperature in a range of 5° C. to 50° C. Thereby, the method of the present invention allows improving irritating odor and whitening.

17 Claims, No Drawings

METHOD FOR PURIFYING ETHYL-2-CYANOACRYLATE ADHESIVE COMPOSITION AND ETHYL-2-CYANOACRYLATE ADHESIVE COMPOSITION

TECHNICAL FIELD

The present invention relates to a method for producing a low whitening and low odor ethyl-2-cyanoacrylate adhesive composition by purification and the low whitening and low odor ethyl-2-cyanoacrylate adhesive composition.

BACKGROUND ART

Cyanoacrylate adhesive compositions each having ethyl-2-cyanoacrylate as a main component are widely used as instant glues, in various industries such as an electronics industry, an electric industry, and an automotive industry, a field of leisure, and general households. This is because such cyanoacrylate adhesive compositions have high anionic polymerizability. Due to such high anionic polymerizability, the cyanoacrylate adhesive compositions each are cured by polymerization and bond various materials in a short period of time by use of anions in water on a surface of a body to be bonded, anions in water in the air, or the like. However, when such an ethyl-2-cyanoacrylate adhesive composition is used, uncured ethyl-2-cyanoacrylate extending out beyond the body to be bonded may cause so-called whitening. In whitening, such uncured ethyl-2-cyanoacrylate may be vaporized. Then, while polymerizing and whitening as a result of polymerization in the vicinity of a bonding section, the ethyl-2-cyanoacrylate adhesive composition is reattached to the body to be bonded. The whitening damages an appearance of the body to be bonded. This whitening tends to occur in the vicinity of a bonding section, in particular, on a plated surface or transparent acrylic resin. This is because bonding a plated surface or transparent acrylic resin is difficult. Moreover, whitening on a bright plated surface or transparent acrylic resin seriously deteriorates commodity value. In addition to whitening, irritating odor caused by vaporized ethyl-2-cyanoacrylate often causes a problem when a large amount of ethyl-2-cyanoacrylate is used.

As a method for solving the above problems, an approach in which alkoxyalkyl-2-cyanoacrylate such as methoxyethyl-2-cyanoacrylate or ethoxyethyl-2-cyanoacrylate is used has been reported (see Patent Literature 1, for example). In this approach, both irritating odor and whitening are improved, however, not sufficiently. Further, this approach has a problem in that alkoxyalkyl-2-cyanoacrylate is much more expensive than ethyl-2-cyanoacrylate. There is another method proposed (see Patent Literature 2, for example). This method employs a monomer having an unsaturated ester. An example of such a monomer is 2-cyanoacrylate derived from hydroxyethyl methacrylate or hydroxypropyl methacrylate. Though such a monomer having an unsaturated ester is odorless and does not cause whitening, the monomer has problems in producibility and storability. This is because the monomer has a functional group having high polymerizability and therefore, is easily polymerized by heat, light, or the like. Furthermore, a compound of such a monomer has another problem. That is, because such a compound strongly irritates skins or the like, special care is required when a material or a product of the compound is handled. In addition, like alkoxyalkyl-2-cyanoacrylate, such a monomer is much more expensive than ethyl-2-cyanoacrylate. Unfortunately, regarding a cyanoacrylate adhesive composition having economically advantageous ethyl-2-cyanoacrylate as a main component, no cyanoacrylate adhesive composition whose irritating odor and whitening are satisfactorily improved has been found so far.

CITATION LIST

Patent Literatures

Patent Literature 1
Japanese Patent Application Publication, Tokukaishou, No. 55-151074 A (Publication Date: Nov. 25, 1980)
Patent Literature 2
Publication of Japanese Translation of PCT International Application, Tokuhyouhei, No. 8-505383 A (Publication Date: Jun. 11, 1996)

SUMMARY OF INVENTION

Technical Problem

An object of present invention is to provide an ethyl-2-cyanoacrylate adhesive composition obtained as a result of significant improvement on above-mentioned conventional problems, that is, irritating odor and whitening of conventional ethyl-2-cyanoacrylate adhesive compositions.

Solution to Problem

In view of the above problems, the inventors of the present invention carried out diligent studies on how decomposition products generated in a production process of ethyl-2-cyanoacrylate influenced whitening and odor. As a result, the inventors found that irritating odor and whitening increased in a case where contents of specific low-boiling-point organic compounds were large. The inventors also found that the irritating odor and whitening were noticeably reduced by lowering the contents of the low-boiling-point organic compounds to predetermined amounts or less than the predetermined amounts, and thereby accomplished the present invention.

In order to solve the above problems, a method of the present invention for purifying an ethyl-2-cyanoacrylate adhesive composition includes the step of arranging a sum total of an acrylonitrile content and an ethanol content to be in a range of 1 ppm to 150 ppm, by carrying out deaeration at the same time as injection of an inactive gas at a reduced pressure in a range of 100 Pa to 10000 Pa at a temperature in a range of 5° C. to 50° C.

Further, in order to solve the above problems, an ethyl-2-cyanoacrylate adhesive composition of the present invention has a sum total of an acrylonitrile content and an ethanol content in a range of 1 ppm to 150 ppm.

Advantageous Effects of Invention

According to the ethyl-2-cyanoacrylate adhesive composition of the present invention, it is possible to provide an ethyl-2-cyanoacrylate adhesive composition whose irritating odor and whitening are significantly improved as compared to conventional ethyl-2-cyanoacrylate adhesive compositions, by controlling contents of specific low-boiling-point organic compounds present in the ethyl-2-cyanoacrylate.

DESCRIPTION OF EMBODIMENTS (I) Ethyl-2-Cyanoacrylate Adhesive Composition

An ethyl-2-cyanoacrylate adhesive composition of the present invention has specific low-boiling-point organic compounds whose contents are controlled so as to be within predetermined ranges. This makes it possible to improve the irritating odor and whitening as compared to irritating odor and whitening of conventional ethyl-2-cyanoacrylate adhesive compositions.

In the present invention, the specific low-boiling-point organic compounds are ethanol and acrylonitrile. Ethanol and acrylonitrile are decomposition products generated in a production process of ethyl-2-cyanoacrylate. In a case where contents of ethanol and acrylonitrile as the decomposition products are reduced, it is possible to obtain a great advantageous effect of improving the irritating odor and whitening. A sum total of an ethanol content and an acrylonitrile content is 150 ppm or less, and more preferably, 100 ppm or less. The ethanol content is 100 ppm or less and more preferably, 50 ppm or less. The acrylonitrile content is 50 ppm or less and more preferably, 20 ppm or less. Though it is difficult to industrially reduce the sum total of the ethanol content and the acrylonitrile content to less than 1 ppm, a sufficient effect can be obtained in a case where the sum total is reduced down to 1 ppm.

In other words, the sum total of the acrylonitrile content and the ethanol content of the ethyl-2-cyanoacrylate adhesive composition of the present invention is preferably in a range of 1 ppm to 150 ppm, and more preferably, in a range of 1 ppm to 100 ppm.

In addition to an arrangement in which the sum total of the acrylonitrile content and the ethanol content is set in the above range, the acrylonitrile content of the ethyl-2-cyanoacrylate adhesive composition of the present invention is preferably 50 ppm or less and more preferably, 20 ppm or less.

Further, in addition to the arrangement in which the sum total of the acrylonitrile content and the ethanol content is set in the above range, in the ethyl-2-cyanoacrylate adhesive composition of the present invention, more preferably, the ethanol content is 100 ppm or less and the acrylonitrile content is 50 ppm or less.

The inventors of the present invention further examined how the decomposition products generated in a production process of ethyl-2-cyanoacrylate influenced whitening on a bright plating and transparent acrylic resin. As a result, the inventors found that by arranging the contents of the above-mentioned low-boiling-point organic compounds within the above ranges, it was possible to obtain advantageous effects such that not only whitening on rubber and odor but also whitening on a plated surface and acrylic resin were reduced.

In other words, in a case where the contents of the low-boiling-point organic compounds in the ethyl-2-cyanoacrylate adhesive composition are reduced to the above ranges, it is possible to reduce not only whitening on rubber and odor but also whitening on a plated surface and acrylic resin.

Terms, the "ethanol content" and the "acrylonitrile content" here indicate values measured and calculated according to the following method.

[Method for Measuring Ethanol Content and Acrylonitrile Content in Ethyl-2-Cyanoacrylate Adhesive Composition]

According to a measurement method, the ethyl-2-cyanoacrylate adhesive composition is sealed in a vial, vaporized, and collected. Then, respective quantities of ethanol and acrylonitrile are determined according to an absolute calibration method with use of reference materials.

<Conditions of Gas Chromatography Measurement>

Apparatus: GC-14A manufactured by SHIMADZU CORPORATION

Column: glass column (outer diameter: 5 mm, inner diameter: 2.6 mm; and length: 3.1 mm)

GC Filler: PEG6000

Column. Temp.: 70° C.

Injection Temperature: 180° C., Detection Temperature: 180° C.

Carrier Gas: helium

<Method for Plotting Calibration Curves>

A sample is prepared by weighing predetermined amounts of acrylonitrile and ethanol, respectively, and adding these acrylonitrile and ethanol to liquid paraffin. Then, 1 g of thus prepared sample is sealed in a 20 ml vial. Then, the sample is exposed for 15 minutes in a thermostat at 100° C. Subsequently, 1 ml of gas phase of the sample is provided for gas chromatography under the above conditions. Calibration curves of ethanol and acrylonitrile are obtained from peak areas obtained, respectively.

<Method for Measuring Ethanol Content and Acrylonitrile Content in Ethyl-2-Cyanoacrylate Adhesive Composition>

The ethyl-2-cyanoacrylate adhesive composition is sealed in a vial. Then, the ethyl-2-cyanoacrylate adhesive composition is exposed under the conditions that are used for plotting the calibration curves. In other words, the ethyl-2-cyanoacrylate adhesive composition is exposed for 15 minutes in a thermostat at 100° C. Then, 1 ml of gas phase of the ethyl-2-cyanoacrylate adhesive composition is provided for gas chromatography under the above conditions.

Respective peaks of ethanol and acrylonitrile are identified from obtained peaks by use of a GCMS and determined. Then, an ethanol content and an acrylonitrile content are calculated by consulting the calibration curves for respective peak areas of ethanol and acrylonitrile. In the present specification, ppm means ppm by weight.

(II) Additives Contained in Ethyl-2-Cyanoacrylate Adhesive Composition

In the ethyl-2-cyanoacrylate adhesive composition of the present invention, a thickening agent may be used in accordance with a purpose. This thickening agent is one that has conventionally been in use and added to an ethyl-2-cyanoacrylate adhesive in addition to ethyl-2-cyanoacrylate that is a main component. The thickening agent may be added and mixed in a range that does not hamper characteristics of the ethyl-2-cyanoacrylate adhesive composition of the present invention. Examples of such a thickening agent encompass: a homopolymer of poly(alkyl methacrylate), a copolymer of different types of methacrylate ester, a copolymer of methacrylate ester and acrylic ester, acrylic rubber, polyurethane rubber, polyester, polyvinyl chloride, polystyrene, cellulose ester, poly(alkyl-α-cyanoacrylate), and an ethylene-vinylacetate copolymer. The above thickening agents may be used solely or in combination of two or more kinds.

Moreover, in the ethyl-2-cyanoacrylate adhesive composition of the present invention, a curing accelerator may be used in accordance with a purpose. This curing accelerator is one that has conventionally been in use and added to an ethyl-2-cyanoacrylate adhesive. The curing accelerator may be added and mixed in a range that does not hamper characteristics of the ethyl-2-cyanoacrylate adhesive composition of the present invention. Examples of such a curing accelerator encompass: polyalcohols, poly alkylene oxide derivatives, crown ethers, and calixarene derivatives.

Further, in the ethyl-2-cyanoacrylate adhesive composition of the present invention, it is possible to use, in accordance with a purpose, a stabilizer (e.g., (a) an anionic polymerization inhibitor such as sulfur dioxide ($SO_2$), methanesulfonic acid, p-toluenesulfonic acid, $BF_3$ ether complex, fluoroboric acid ($HBF_4$), and trialkylborate, and (b) a radical polymerization inhibitor such as hydroquinone, hydroquinone monomethyl ether, t-butylcatechol, catechol, and pyrogallol), a plasticizer (e.g., dimethyl phthalate, diethyl phthalate, diisodecyl phthalate, and acetyl tributyl citrate), a coloring agent, a perfume, a solvent, a strength improving agent, aliphatic polycarboxylic acid, and aromatic polycarboxylic acid. These substances are ones that have conventionally been in use and added to an ethyl-2-cyanoacrylate adhesive. These substances may be added and mixed in a range that does not hamper effects of the present invention. Note that in the present specification, $BF_3$ ether complex indicates a complex of $BF_3$ and an ether such as dimethyl ether, diethyl ether, di-n-propyl ether, di-iso-propyl ether, or tetrahydrofuran.

Furthermore, the inventors of the present invention found that, by adding a specific additive as an additive mentioned above at a predetermined amount to the ethyl-2-cyanoacrylate adhesive composition whose low-boiling-point organic compounds mentioned above were reduced to the above ranges, it was possible to obtain a better effect of reducing irritating odor and whitening.

<$HBF_4$, $BF_3$ Ether Complex and $SO_2$>

In other words, in the ethyl-2-cyanoacrylate adhesive composition whose low-boiling-point organic compounds mentioned above are reduced to the above ranges, an effect of reducing whitening on acrylic resin can be improved by using $HBF_4$, $BF_3$ ether complex and/or $SO_2$ as an additive at an amount in a predetermined range. The additives mentioned above are generally added as stabilizers.

In a case where one or a combination of $HBF_4$ and $BF_3$ ether complex is added, a total content of the one or the combination of $HBF_4$ and $BF_3$ ether complex is preferably in a range of 1 ppm to less than 20 ppm. That is, the ethyl-2-cyanoacrylate adhesive composition of the present invention may contain $HBF_4$ and/or $BF_3$ ether complex preferably at a total content in a range of 1 ppm to less than 20 ppm, more preferably at a total content in a range of 1 ppm to 15 ppm, and most preferably at a total content in a range of 1 ppm to 10 ppm. The total content of $HBF_4$ and/or $BF_3$ ether complex is preferably 1 ppm or more, because $HBF_4$ and/or $BF_3$ ether complex is effective as a stabilizer at such a total content. Moreover, in a case where the total content of $HBF_4$ and/or $BF_3$ ether complex is less than 20 ppm, $HBF_4$ and/or $BF_3$ ether complex is effective as a stabilizer. Further, in this case, the ethyl-2-cyanoacrylate adhesive composition is cured within a moderate period of time and the ethyl-2-cyanoacrylate adhesive does not spread around. This makes it possible to prevent whitening.

In a case where $SO_2$ is added, an $SO_2$ content is preferably in a range of 30 ppm to 100 ppm, and more preferably, in a range of 40 ppm to 80 ppm. Here, $SO_2$ may contribute to stabilization of gas phase. Accordingly, vapor of cyanoacrylate from an adhesive extending beyond a section where the adhesive is to be applied may not be cured immediately. As a result, the adhesive may moderately spread. This may prevent whitening. At the SO2 content of ppm or more, the vapor of the adhesive beyond the section where the adhesive is to be applied does not easily polymerize and therefore the SO2 content of 30 ppm or more is preferable. In a case where the SO2 content is 100 ppm or less, an excellent curing speed is obtained. This curing speed indicates basic performance of an instant glue. Therefore, the SO2 content of 100 ppm or less is preferable.

<Crown Ethers and Calixarene Derivatives>

In the ethyl-2-cyanoacrylate adhesive composition of the present invention in which the low-boiling-point organic compounds are reduced to the above ranges, an effect of reducing whitening can be further enhanced by (i) using crown ethers, calixarene derivatives, or the like as additives and (ii) setting an amount of the additives in a predetermined range. These additives are generally added as curing accelerators.

The crown ethers are not specifically limited. Examples of the crown ethers encompass 12-crown-4-ether, 15-crown-5-ether, and 18-crown-6-ether.

Further, the calixarene derivatives are not specifically limited. Examples of the calixarene derivatives encompass calixarene derivatives disclosed in Japanese Patent Application Publication, Tokukaishou, No. 60-179482 A, Japanese Patent Application Publication, Tokukaishou, No. 62-235379 A, Japanese Patent Application Publication, Tokukaishou, No. 63-88152 A, and the like. Examples of particularly suitable calixarene derivatives encompass: 5,11,17,23,29,35-hexatertiarybutyl-37,38,39,40,41,42-hexa(2-ethoxy-2-oxoethoxy)calix(6)arene, and 5,11,17,23-tetratertiarybutyl-25,26,27,28-tetra(2-ethoxy-2-oxoethoxy)calix(4)arene.

The above additives may be solely used or in combination of two or more kinds. An amount of these additives to be added is preferably in a range of 50 ppm to 5000 ppm, more preferably in a range of 100 ppm to 2000 ppm, and most preferably, in a range of 200 ppm to 1000 ppm. In other words, the ethyl-2-cyanoacrylate adhesive composition of the present invention may contain at least one compound from a group of crown ethers and calixarene derivatives, preferably at a total content in a range of 50 ppm to 5000 ppm, more preferably at a total content in a range of 100 ppm to 2000 ppm, and most preferably at a total content in a range of 200 ppm to 1000 ppm.

In a case where at least one compound from the group of crown ethers and calixarene derivatives is contained at a total content of 50 ppm or more, it is possible to obtain an excellent effect of accelerating curing of an adhesive extending beyond a section where the adhesive is to be applied. As a result, an effect of reducing whitening can be further enhanced. Moreover, in a case where at least one compound from the group of crown ethers and calixarene derivatives is contained at a total content of 5000 ppm or less, a speed of curing does not become too fast. Accordingly, an amount of heat generated in curing does not become too large. As a result, vaporization of cyanoacrylate that is a cause of whitening can be suppressed. Therefore, an excellent effect of reducing whitening can be obtained.

<Phthalate Esters and Acetyl Citrate Esters>

In the ethyl-2-cyanoacrylate adhesive composition of the present invention in which the low-boiling-point organic compounds are reduced to the above ranges, an effect of reducing whitening can be enhanced by (i) using phthalate esters, acetyl citrate esters, or the like as additives according to need and (ii) arranging an amount of the additives within a predetermined range. The above additives are generally added as plasticizers.

Examples of phthalate esters encompass dimethyl phthalate, diethyl phthalate, dibutyl phthalate, and diisodecyl phthalate. Examples of acetyl citrate esters encompass acetyl triethyl citrate, and acetyl tributyl citrate.

The above additives may be used solely or in combination of two or more kinds. An amount of these additives to be added is preferably in a range of 5% by weight to 40% by weight, and more preferably in a range of 10% by weight to 30% by weight, with respect to a weight of ethyl-2-cyanoacrylate that is a main component of the ethyl-2-cyanoacrylate adhesive composition. In other words, the ethyl-2-cyanoacrylate adhesive composition of the present invention may contain at least one compound from a group of phthalate esters and acetyl citrate esters, and a total content of the at least one compound is preferably in a range of 5% by weight to 40% by weight and more preferably in a range of 10% by weight to 30% by weight, with respect to a weight of ethyl-2-cyanoacrylate that is a main component of the ethyl-2-cyanoacrylate adhesive composition.

In a case where at least one compound from a group of phthalate esters and acetyl citrate esters is contained at a total content of 5% by weight or more, a plasticizing effect is obtained. Therefore, it is preferable to contain the at least one compound at a total content of 5% by weight or more. Moreover, in a case where at least one compound from a group of phthalate esters and acetyl citrate esters is contained at a total content of 40% by weight or less, deceleration of a speed of curing is suppressed. Therefore, in this case, an excellent effect of reducing whitening can be obtained.

<Multisubstituted Benzenes>

In the ethyl-2-cyanoacrylate adhesive composition of the present invention in which the low-boiling-point organic compounds are reduced to the above ranges, an effect of reducing whitening on a plated surface can be further enhanced by (i) using, as an additive, at least one compound that is a multi-substituted benzene represented by General Formula (1) below and (ii) arranging a total amount of the additive in a predetermined range.

[Chem. 1]

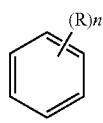

(1)

In General Formula (1) above, R represents one or a combination of two or more kinds of a carboxyl group, a carboxylic anhydride, an aldehyde group, a hydroxyl group, a carboxylic acid ester group, and an alkoxy group; and n is an integer in a range of 2 to 6. Note that polycarboxylic acid ester is excluded here.

More specifically, examples of the above at least one compound encompass: phthalic acid, trimellitic acid, pyromellitic acid, phthalic anhydride, trimellitic anhydride, pyromellitic dianhydride, terephthalaldehyde, catechol, pyrogallol, tetrahydroxybenzene, hexahydroxybenzene, salicylic acid, gallic acid, and gallic acid methyl ester. In particular, trimellitic acid, trimellitic anhydride, salicylic acid, gallic acid, or pyrogallol is preferable as the at least one compound. The above additives may be used solely or in combination of two or more kinds. A total amount of the at least one compound to be added is preferably in a range of 10 ppm to 5000 ppm, more preferably in a range of 50 ppm to 2000 ppm, and most preferably in a range of 100 ppm to 800 ppm. In other words, the ethyl-2-cyanoacrylate adhesive composition of the present invention may contain at least one compound represented by General Formula (1) above, and a total content of the at least one compound is preferably in a range of 10 ppm to 5000 ppm, more preferably in a range of 50 ppm to 2000 ppm, and most preferably in a range of 100 ppm to 800 ppm.

By containing the at least one compound represented by the General Formula (1) above at a total content in a range of 10 ppm to 5000 ppm, an effect of reducing whitening on a plated surface can be further enhanced.

<Hydrophobic Silica>

In the ethyl-2-cyanoacrylate adhesive composition of the present invention in which the low-boiling-point organic compounds are reduced to the above ranges, an effect of reducing whitening can be further enhanced by (i) using hydrophobic silica as an additive and (ii) setting an amount of the hydrophobic silica to be added in a predetermined range. The hydrophobic silica here has pH in a range of 4 to 7 in a case where the hydrophobic silica is dispersed at 4% by weight in a solution having a proportion of water/methanol=1:1 (wt/wt). This additive is added as, for example, a thixotropic agent.

An amount of the hydrophobic silica to be added is more preferably in a range of 1% by weight to 15% by weight, and most preferably in a range of 3% by weight to 10% by weight, with respect to a weight of ethyl-2-cyanoacrylate that is a main component of the ethyl-2-cyanoacrylate adhesive composition. In other words, the ethyl-2-cyanoacrylate adhesive composition of the present invention may contain the hydrophobic silica having pH in a range of 4 to 7 in a case where the hydrophobic silica is dispersed at 4% by weight in a solution having a proportion of water/methanol=1:1 (wt/wt). Here, the ethyl-2-cyanoacrylate adhesive composition of the present invention may contain the hydrophobic silica more preferably at a content of 1% by weight to 15% by weight, and most preferably at a content of 3% by weight to 10% by weight with respect to a weight of ethyl-2-cyanoacrylate. In a particularly preferable case, the ethyl-2-cyanoacrylate adhesive composition of the present invention contains the hydrophobic silica having pH in a range of 5 to 6 in a case where the hydrophobic silica is dispersed at 4% by weight in a solution having a proportion of water/methanol=1:1 (wt/wt). In this particularly preferable case, the ethyl-2-cyanoacrylate adhesive composition contains the hydrophobic silica at a content of 3% by weight to 10% by weight. As a result, in this particularly preferable case, an effect of reducing whitening can be further enhanced. Examples of the hydrophobic silica satisfying above-mentioned conditions encompass RY200S manufactured by Nippon Aerosil Co. Ltd., and hydrophobic silica that is manufactured by Degussa Corporation or Cabot Corporation and that satisfies the above-mentioned conditions.

(III) Method For Purifying Ethyl-2-Cyanoacrylate Adhesive Composition

As a method for reducing the above-mentioned low-boiling-temperature organic compounds in the ethyl-2-cyanoacrylate adhesive composition, generally purification by distillation is considered. However, by using a method employing simple distillation, it is difficult to remove the low-boiling-point organic compounds. In a distillation method using a tray column or packed column, ethyl-2-cyanoacrylate is exposed to a high temperature for a long time. This results in decomposition reaction of ethyl-2-cyanoacrylate during distillation. Consequently, decomposition products, such as ethanol and acrylonitrile, generated as a result of the decomposition reaction tend to increase. Accordingly, for reducing ethanol and acrylonitrile that are the specific low-boiling-point organic compounds of the present invention, it is necessary to take a method in which such decomposition products are not easily produced. As examples of such a method, the following methods are considered: (a) a method in which the low-boiling-point organic compounds, such as ethanol and acrylonitrile that are decomposition products of ethyl-2-cyanoacrylate, are effectively removed by (i) injecting nitrogen under a condition at a reduced pressure in which thermal exposure is lower and (ii) deaerating by bubbling; and (b) a method in which deaeration by bubbling is carried out with respect to ethyl-2-cyanoacrylate that has been obtained in distillation by removing a first fraction containing the low-boiling-point organic substances.

Regarding a deaeration method, deaeration is carried out by (i) injecting an inactive gas generally at a reduced pressure in a range of 100 Pa to 10000 Pa, preferably at a reduced pressure in a range of 200 Pa to 5000 Pa, and more preferably at a reduced pressure in a range of 300 Pa to 2000 Pa and (ii) bubbling. In a case where the reduced pressure is less than 100 Pa, cyanoacrylate monomers may become distillates unless a deaeration temperature is set at 5° C. or lower. Meanwhile, in a case where the reduced pressure is higher than 10000 Pa, bubbling decreases unless the deaeration temperature is set at 50° C. or higher. In the above cases, performance of removing ethanol and acrylonitrile tends to deteriorate. The deaeration temperature is generally at 5° C. to 50° C., preferably at 10° C. to 45° C., and more preferably at 15° C. to 40° C. In a case where the deaeration temperature is at lower than 5° C., economical efficiency is hampered because time needs to be taken for temperature control. Meanwhile, in a case where the deaeration temperature is set at higher than 50° C., a decomposition reaction occurs during deaeration. As a result, in the above cases, performance of removing ethanol and acrylonitrile tends to deteriorate. A deaeration time and a flow rate of the inactive gas depend on a scale of distillation. The following explains a deaeration time and a flow rate of the inactive gas in bubbling at a reduced pressure, for each kg of ethyl-2-cyanoacrylate obtained in distillation by removal of a first fraction including the low-boiling point compounds. The inactive gas such as nitrogen gas is injected generally at a flow rate in a range of 0.01 L/min to 100 L/min, more preferably at a flow rate in a range of 0.05 L/min to 50 L/min, and more preferably at a flow rate in a range of 0.1 L/min to 20 L/min. The deaeration time is generally in a range of 1 hour to 50 hours, preferably in a range of 3 hours to 30 hours, and more preferably 5 hours to 24 hours. In a case where the flow rate of the inactive gas is lower than the flow rate generally used and/or the deaeration time is shorter than the deaeration time generally used, performance of removing ethanol and acrylonitrile tends to deteriorate. Meanwhile, in a case where the flow rate of the inactive gas is higher than the flow rate generally used and/or the deaeration time is longer than the deaeration time generally used, a decomposition reaction occurs during deaeration and consequently, performance of removing ethanol and acrylonitrile tends to deteriorate. By using the above deaeration method, the following becomes possible in the ethyl-2-cyanoacrylate adhesive composition: (a) a sum total of an acrylonitrile content and an ethanol content is suppressed to 150 ppm or less; (b) the ethanol content is suppressed to 100 ppm or less; or (c) the acrylonitrile content is suppressed to 50 ppm or less. As a result, it becomes possible to noticeably reduce irritating odor and whitening of the ethyl-2-cyanoacrylate adhesive composition.

In other words, the present invention provides the followings (1) to (14).

[1] A method for purifying an ethyl-2-cyanoacrylate adhesive composition, the method including the step of arranging a sum total of an acrylonitrile content and an ethanol content to be in a range of 1 ppm to 150 ppm, by carrying out deaeration at the same time as injection of an inactive gas at a reduced pressure in a range of 100 Pa to 10000 Pa at a temperature in a range of 5° C. to 50° C.

[2] An ethyl-2-cyanoacrylate adhesive composition having a sum total of an acrylonitrile content and an ethanol content in a range of 1 ppm to 150 ppm.

[3] The ethyl-2-cyanoacrylate adhesive composition as set forth in [2], wherein the acrylonitrile content is 50 ppm or less.

[4] The ethyl-2-cyanoacrylate adhesive composition as set forth in [2], wherein: the ethanol content is 100 ppm or less; and the acrylonitrile content is 50 ppm or less.

[5] The ethyl-2-cyanoacrylate adhesive composition as set forth in any one of [2] to [4], further including $SO_2$, wherein a content of the $SO_2$ is in a range of 30 ppm to 100 ppm.

[6] The ethyl-2-cyanoacrylate adhesive composition as set forth in any one of [2] to [4], further including $HBF_4$ and/or $BF_3$ ether complex, wherein a total content of the $HBF_4$ and/or the $BF_3$ ether complex is in a range of 1 ppm to less than 20 ppm.

[7] The ethyl-2-cyanoacrylate adhesive composition as set forth in any one of [2] to [4], further including at least one compound from a group of crown ethers and calixarene derivatives, wherein a total content of the at least one compound is in a range of 50 ppm to 5000 ppm.

[8] The ethyl-2-cyanoacrylate adhesive composition as set forth in any one of [2] to [4], further including at least one compound from a group of phthalate esters and acetyl citrate esters, wherein a total content of the at least one compound is in a range of 5% by weight to 40% by weight.

[9] The ethyl-2-cyanoacrylate adhesive composition as set forth in any one of [2] to [4], further including at least one compound represented by a general formula (1):

[Chem. 2]

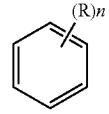

(1)

wherein: R represents one or a combination of two or more kinds of a carboxyl group, a carboxylic anhydride, an aldehyde group, a hydroxyl group, an alkoxy group and a carboxylic acid ester group excluding polycarboxylic acid ester; and n is an integer in a range of 2 to 6, wherein a total content of the at least one compound is in a range of 10 ppm to 5000 ppm.

[10] The ethyl-2-cyanoacrylate adhesive composition as set forth in any one of [2] to [4], further including hydrophobic silica, the hydrophobic silica having pH in a range of 4 to 7 in a case where the hydrophobic silica is dispersed at 4% by weight in a solution having a proportion of water/methanol=1:1 (wt/wt), wherein a content of the hydrophobic silica is in a range of 1% by weight to 10% by weight.

[11] The ethyl-2-cyanoacrylate adhesive composition as set forth in any one of [7] to [10], further including $SO_2$, wherein a content of the $SO_2$ is in a range of 30 ppm to 100 ppm.

[12] The ethyl-2-cyanoacrylate adhesive composition as set forth in any one of [7] to [10], further including $HBF_4$ and/or $BF_3$ ether complex, wherein a total content of the $HBF_4$ and/or the $BF_3$ ether complex is in a range of 1 ppm to less than 20 ppm.

[13] The ethyl-2-cyanoacrylate adhesive composition as set forth in any one of [7] to [12], wherein the sum total of the acrylonitrile content and the ethanol content is in a range of 1 ppm to 100 ppm.

EXAMPLES

The following explains in more detail the present invention by providing examples and comparative examples. However, the present invention is by no means limited by the following examples and comparative examples. Note that in the present examples, a whitening test and an odor sensing test were carried out according to the following method.

[Whitening Test]
(1) Whitening on Rubber Surface
0.1 g of an ethyl-2-cyanoacrylate adhesive composition was introduced into a 50 ml polyethylene container, and the container was covered with an NBR plate. Then, after one-day curing, a degree of whitening on the NBR plate was visually checked.

(2) Whitening on Plated Surface 1 g of the ethyl-2-cyanoacrylate adhesive composition was applied to chrome-plated steel test pieces of 1.6×25 100 mm. Then, the chrome-plated steel test pieces were overlapped and bonded each other. Immediately after the bonding, a fingerprint was put on a surface of the chrome-plated steel test pieces bonded. Then, the chrome-plated steel test pieces were put into a 250 ml polyethylene container and the polyethylene container was covered with a lid. After one-day curing, a degree of whitening at a section where the fingerprint had been put was visually checked.

(3) Whitening on Acrylic Resin Plate Surface 1 g of the ethyl-2-cyanoacrylate adhesive composition was applied to acrylic test pieces of 2.0×25×100 mm. Then, the acrylic test pieces were overlapped and bonded each other. Immediately after the bonding, a fingerprint was put on a surface of the acrylic test pieces bonded. Then, the acrylic test pieces were put into a 250 ml polyethylene container and the polyethylene container was covered with a lid. After one-day curing, a degree of whitening at a section where the fingerprint had been put was visually checked.

(4) Criteria for Evaluation

A case where whitening was hardly observed was evaluated as "GOOD"; a case where light whitening was observed was evaluated as "FAIR"; and a case where heavy whitening was observed was evaluated as "POOR". Note that "GOOD—FAIR" in tables means that whitening was observed more than in the case evaluated as "GOOD" but the whitening was lighter as compared to the case evaluated as "FAIR".

[Odor Sensing Test]

0.1 g of the ethyl-2-cyanoacrylate adhesive composition was put in a 50 ml polyethylene container and the polyethylene container was covered with a lid. After ten minutes, the 50 ml polyethylene container was opened and five testers evaluated odor. Among evaluations "GOOD", "FAIR", and "POOR", a level selected by the largest number of testers was adopted.

Note that: a case where odor was hardly sensed was evaluated as "GOOD"; a case where odor was slightly sensed was evaluated as "FAIR"; and a case where odor was severely sensed was evaluated as "POOR".

Synthesis Example 1

Synthesis of Crude Ethyl-2-Cyanoacrylate 60 parts of paraformaldehyde, 200 parts of toluene, 0.2 part of piperidine were introduced into a three-neck flask having a stirrer, a thermometer, a water separator, and a dropping funnel, and kept at a temperature of 80° C. to 90° C. While stirring was carried out, 226 parts of cyanoacetic ester were dropped. For this dropping, 60 minutes was taken. After the dropping was completed, generated water was refluxed while azeotropic separation was carried out. Then, paraformaldehyde, toluene, piperidine and cyanoacetic ester were reacted for approximately 6 hours until a theoretical amount of water became distillate. As a result, toluene solution containing a polymer was obtained. After this solution was desolventized at an atmospheric pressure, 30 parts of tricresyl phosphate, 6 parts of phosphorus pentoxide, and 3 parts of hydroquinone were added and mixed well. After a resultant mixture was desolvatized at a reduced pressure, the resultant mixture was heated to a temperature of 170° C. to 200° C. at a pressure of 400 Pa so that depolymerization was carried out. As a result, 212 parts of crude ethyl-2-cyanoacrylate were obtained. With respect to 100 parts of thus obtained crude ethyl-2-cyanoacrylate, 0.5 part of hydroquinone, 0.1 part of phosphorus pentoxide, and 0.005 part of $BF_3$ complex (boron trifluoride diethyl ether complex) were added as polymerization inhibitors. Then, distillation was carried out at a temperature in a range of 35° C. to 90° C. at a reduced pressure in a range of 133 Pa to 400 Pa. For removing low-boiling-point components, 3% by weight of thus distilled material (with respect to a full weight of the crude ethyl-2-cyanoacrylate) was removed as a first fraction. Subsequently, 90% by weight of distilled material (with respect to the full weight of the crude ethyl-2-cyanoacrylate) was obtained as a main fraction of distillate. As a result, purified ethyl-2-cyanoacriylate monomers were obtained. With respect to 100 parts by weight of this purified ethyl-2-cyanoacrylate monomers, 0.001 part by weight of fluoroboric acid and 0.1 part by weight of hydroquinone were added. As a result, an ethyl-2-cyanoacrylate adhesive composition was prepared.

Synthesis Example 2

Synthesis of Crude Ethyl-2-Cyanoacrylate 60 parts of paraformaldehyde, 200 parts of toluene, 0.2 part of piperidine were introduced into a three-neck flask having a stirrer, a thermometer, a water separator, and a dropping funnel, and kept at a temperature of 80° C. to 90° C. While stirring was carried out, 226 parts of cyanoacetic ester were dropped. For this dropping, 60 minutes was taken. After the dropping was completed, generated water was refluxed while azeotropic separation was carried out. Then, paraformaldehyde, toluene, piperidine and cyanoacetic ester were reacted for approximately 6 hours until a theoretical amount of water became distillate. As a result, toluene solution containing a polymer was obtained. After this solution was desolventized at an atmospheric pressure, 30 parts of tricresyl phosphate, 6 parts of phosphorus pentoxide, and 3 parts of hydroquinone were added and mixed well. After a resultant mixture was desolvatized at a reduced pressure, the resultant mixture was heated to a temperature of 170° C. to 200° C. at a pressure of 400 Pa so that depolymerization was carried out. As a result, 212 parts of crude ethyl-2-cyanoacrylate were obtained. With respect to 100 parts of thus obtained crude ethyl-2-cyanoacrylate, 0.5 part of hydroquinone, 0.1 part of phosphorus pentoxide, and 0.005 part of $BF_3$ complex (boron trifluoride diethyl ether complex) were added as polymerization inhibitors. Then, distillation was carried out at a temperature in a range of 35° C. to 90° C. at a reduced pressure in a range of 133 Pa to 400 Pa. For removing low-boiling-point components, 3% by weight of thus distilled material (with respect to a full weight of the crude ethyl-2-cyanoacrylate) was removed as a first fraction. Subsequently, 90% by weight of distilled material (with respect to the full weight of the crude ethyl-2-cyanoacrylate) was obtained as a main fraction of distillate. As a result, purified ethyl-2-cyanoacriylate monomers were obtained. With respect to 100 parts by weight of this purified ethyl-2-cyanoacrylate monomers, 0.002 part by weight of $SO_2$ was added. As a result, an ethyl-2-cyanoacrylate adhesive composition was prepared.

Example 1

While nitrogen was injected (2 L/min) at a reduced pressure of 666 Pa, 1 kg of the ethyl-2-cyanoacrylate adhesive composition obtained in Synthesis Example 1 was deaerated for 24 hours at a temperature of 30° C. Then, a sample was collected and subjected to a whitening test, an order sensing test, and measurement of an ethanol content and an acrylonitrile content. Table 1 shows a result of Example 1.

Example 2

While nitrogen was injected (2 L/min) at a reduced pressure of 1330 Pa, 1 kg of the ethyl-2-cyanoacrylate adhesive composition obtained in Synthesis Example 1 was deaerated for 24 hours at a temperature of 30° C. Then, a sample was collected and subjected to a whitening test, an order sensing test, and measurement of an ethanol content and an acrylonitrile content. Table 1 shows a result of Example 2.

Example 3

While nitrogen was injected (2 L/min) at a reduced pressure of 666 Pa, 1 kg of the ethyl-2-cyanoacrylate adhesive composition obtained in Synthesis Example 1 was deaerated for 24 hours at a temperature of 45° C. Then, a sample was collected and subjected to a whitening test, an order sensing test, and measurement of an ethanol content and an acrylonitrile content. Table 1 shows a result of Example 3.

Example 4

While nitrogen was injected (2 L/min) at a reduced pressure of 666 Pa, 1 kg of the ethyl-2-cyanoacrylate adhesive composition obtained in Synthesis Example 1 was deaerated for 4 hours at a temperature of 30° C. Then, a sample was collected and subjected to a whitening test, an order sensing test, and measurement of an ethanol content and an acrylonitrile content. Table 1 shows a result of Example 4.

Example 5

While nitrogen was injected (2 L/min) at a reduced pressure of 1330 Pa, 1 kg of the ethyl-2-cyanoacrylate adhesive composition obtained in Synthesis Example 1 was deaerated for 4 hours at a temperature of 40° C. Then, a sample was collected and subjected to a whitening test, an order sensing test, and measurement of an ethanol content and an acrylonitrile content. Table 1 shows a result of Example 5.

carried out. Table 2 shows a result of Example 6. An ethanol content and an acrylonitrile content are the same as those in Example 2.

Example 7

While nitrogen was injected (2 L/min) at a reduced pressure of 1330 Pa, 1 kg of the ethyl-2-cyanoacrylate adhesive composition that was obtained in Synthesis Example 2 was deaerated for 24 hours at a temperature of 30° C. Then, to this ethyl-2-cyanoacrylate adhesive composition obtained as a result of deaeration, $SO_2$ was added and an ethyl-2-cyanoacrylate adhesive composition was prepared so that a content of $SO_2$ was 20 ppm. Then, a sample of this ethyl-2-cyanoacrylate adhesive composition was collected and subjected to a whitening test, an order sensing test, and measurement of an ethanol content and an acrylonitrile content. Table 2 shows a result of Example 7.

Example 8

To the ethyl-2-cyanoacrylate adhesive composition that was obtained in Example 7 and that had been deaerated, $SO_2$ was added and an ethyl-2-cyanoacrylate adhesive composition was prepared so that a content of $SO_2$ was 40 ppm. Then, a sample of this ethyl-2-cyanoacrylate adhesive composition was collected and subjected to a whitening test and an order sensing test. Table 2 shows a result of Example 8. An ethanol content and an acrylonitrile content are the same as those in Example 7.

Example 9

To the ethyl-2-cyanoacrylate adhesive composition that was obtained in Example 7 and that had been deaerated, $SO_2$ was added and an ethyl-2-cyanoacrylate adhesive composi-

TABLE 1

|  | EXAMPLES | | | | | COMPARATIVE EXAMPLES | |
|---|---|---|---|---|---|---|---|
|  | 1 | 2 | 3 | 4 | 5 | 1 | 2 |
| ETHANOL CONTENT (ppm) | 20 | 60 | 40 | 90 | 80 | 180 | 300 |
| ACRYLONITRILE CONTENT (ppm) | 10 | 30 | 10 | 20 | 40 | 100 | 200 |
| SUM TOTAL (ppm) OF ETHANOL CONTENT AND ACRYLONITRILE CONTENT | 30 | 90 | 50 | 110 | 120 | 280 | 500 |
| $SO_2$ (ppm) |  |  |  |  |  |  |  |
| $HBF_4$ (ppm) | 10 | 10 | 10 | 10 | 10 | 10 | 10 |
| CROWN ETHER (ppm) |  |  |  |  |  |  |  |
| CALIXARENE (ppm) |  |  |  |  |  |  |  |
| DIMETHYL PHTHALATE (% BY WEIGHT) |  |  |  |  |  |  |  |
| HYDROPHOBIC SILICA (% BY WEIGHT) |  |  |  |  |  |  |  |
| TRIMELLITIC ACID (ppm) |  |  |  |  |  |  |  |
| SALICYLIC ACID (ppm) |  |  |  |  |  |  |  |
| GALLIC ACID (ppm) |  |  |  |  |  |  |  |
| PYROGALLOL (ppm) |  |  |  |  |  |  |  |
| ODOR SENSING TEST | GOOD | GOOD | GOOD | FAIR | FAIR | POOR | POOR |
| WHITENING TEST (RUBBER) | GOOD | GOOD | GOOD | GOOD | FAIR | POOR | POOR |
| WHITENING TEST (PLATING) | FAIR | FAIR | FAIR | FAIR | FAIR | POOR | POOR |
| WHITENING TEST (ACRYLIC RESIN) | GOOD | GOOD | GOOD | FAIR | FAIR | POOR | POOR |

Example 6

To an ethyl-2-cyanoacrylate adhesive composition that was obtained in Example 2 and that had been deaerated, 0.001 part by weight of fluoroboric acid was further added and mixed. Then, a whitening test and an odor sensing test were tion was prepared so that a content of $SO_2$ was 200 ppm. Then, a sample of this ethyl-2-cyanoacrylate adhesive composition was collected and subjected to a whitening test and an order sensing test. Table 2 shows a result of Example 9. An ethanol content and an acrylonitrile content are the same as those in Example 7.

Examples 10 to 12

To an ethyl-2-cyanoacrylate adhesive composition that was obtained in Example 4 and that had been deaerated, 18-crown-6-ether was added and mixed so that respective contents of 18-crown-6-ether were 40 ppm, 500 ppm, and 10000 ppm. Then, respective samples of thus prepared ethyl-2-cyanoacrylate adhesive compositions were collected and subjected to a whitening test and an order sensing test. Table 2 shows results of Examples 10 to 12. An ethanol content and an acrylonitrile content in each of Examples 10 to 12 are the same as those in Example 4.

Example 13

To the ethyl-2-cyanoacrylate adhesive composition that was obtained in Example 4 and that had been deaerated, 5,11,17,23-tetratertiarybutyl-25,26,27,28-tetra(2-ethoxy-2-oxoethoxy)calix(4)arene was added and mixed so that a content of 5,11,17,23-tetratertiarybutyl-25,26,27,28-tetra(2-ethoxy-2-oxoethoxy)calix(4)arene was 1000 ppm. Then, a sample of thus prepared ethyl-2-cyanoacrylate adhesive composition was collected and subjected to a whitening test and an order sensing test. Table 2 shows a result of Example 13. An ethanol content and an acrylonitrile content are the same as those in Example 4.

Example 14 and 15

To the ethyl-2-cyanoacrylate adhesive composition that was prepared in Example 7 so that the content of $SO_2$ was 20 ppm, dimethyl phthalate was added and mixed so that contents of dimethyl phthalate were 20% by weight and 45% by weight each with respect to a total weight of each ethyl-2-cyanoacrylate adhesive composition to be prepared here. Then, respective samples of thus obtained ethyl-2-cyanoacrylate adhesive compositions were collected and subjected to a whitening test and an order sensing test. Table 3 shows results of Examples 14 and 15. In Example 14, an ethanol content was 50 ppm and an acrylonitrile content was 25 ppm. In Example 15, an ethanol content was 40 ppm and an acrylonitrile content was 20 ppm.

Examples 16 and 17

To the ethyl-2-cyanoacrylate adhesive composition that was prepared in Example 7 so that the content of $SO_2$ was 20 ppm, hydrophobic silica was added and mixed so that contents of the hydrophobic silica were 5% by weight and 20% by weight each with respect to a total weight of each ethyl-2-cyanoacrylate adhesive composition to be prepared here. The hydrophobic silica here has pH in a range of 5 to 6 in a case where the hydrophobic silica is dispersed at 4% by

TABLE 2

| | EXAMPLES | | | | | | | | COMPARATIVE EXAMPLE |
|---|---|---|---|---|---|---|---|---|---|
| | 6 | 7 | 8 | 9 | 10 | 11 | 12 | 13 | 3 |
| ETHANOL CONTENT (ppm) | 60 | 60 | 60 | 60 | 90 | 90 | 90 | 90 | 60 |
| ACRYLONITRILE CONTENT (ppm) | 30 | 30 | 30 | 30 | 20 | 20 | 20 | 20 | 120 |
| SUM TOTAL (ppm) OF ETHANOL CONTENT AND ACRYLONITRILE CONTENT | 90 | 90 | 90 | 90 | 110 | 110 | 110 | 110 | 180 |
| $SO_2$ (ppm) | | 20 | 40 | 200 | | | | | 40 |
| $HBF_4$ (ppm) | 20 | | | | 10 | 10 | 10 | 10 | |
| CROWN ETHER (ppm) | | | | | 40 | 500 | 10000 | | |
| CALIXARENE (ppm) | | | | | | | | 1000 | 1000 |
| DIMETHYL PHTHALATE (% BY WEIGHT) | | | | | | | | | |
| HYDROPHOBIC SILICA (% BY WEIGHT) | | | | | | | | | |
| TRIMELLITIC ACID (ppm) | | | | | | | | | |
| SALICYLIC ACID (ppm) | | | | | | | | | |
| GALLIC ACID (ppm) | | | | | | | | | |
| PYROGALLOL (ppm) | | | | | | | | | |
| ODOR SENSING TEST | GOOD | GOOD | GOOD | GOOD | FAIR | FAIR | FAIR | FAIR | POOR |
| WHITENING TEST (RUBBER) | FAIR | GOOD | GOOD | FAIR | GOOD | GOOD | GOOD/FAIR | GOOD | POOR |
| WHITENING TEST (PLATING) | FAIR | FAIR | FAIR | FAIR | FAIR | FAIR | FAIR | FAIR | POOR |
| WHITENING TEST (ACRYLIC RESIN) | FAIR | FAIR | GOOD | FAIR | FAIR | GOOD | FAIR | GOOD | POOR | weight in a solution having a proportion of water/methanol=1:1 (wt/wt). Then, respective samples of ethyl-2-cyanoacrylate adhesive compositions thus obtained were collected and subjected to a whitening test and an order sensing test. Table 3 shows results of Examples 16 and 17. In Example 16, an ethanol content was 57 ppm and an acrylonitrile content was 29 ppm. In Example 17, an ethanol content was 50 ppm and an acrylonitrile content was 25 ppm.

Example 18

To the ethyl-2-cyanoacrylate adhesive composition that was prepared in Example 7 so that the content of $SO_2$ was 20 ppm, salicylic acid was added and mixed so that a content of salicylic acid was 400 ppm. Then, a sample of an ethyl-2-cyanoacrylate adhesive composition thus obtained was collected and subjected to a whitening test and an order sensing test. Table 3 shows a result of Example 18. An ethanol content and an acrylonitrile content are the same as those in Example 7.

Example 19

To the ethyl-2-cyanoacrylate adhesive composition that was obtained in Example 4 and that had been deaerated, salicylic acid was added and mixed so that a content of salicylic acid was 1000 ppm. Then, a sample of this ethyl-2-cyanoacrylate adhesive composition was collected and subjected to a whitening test and an order sensing test. Table 3 shows a result of Example 19. An ethanol content and an acrylonitrile content are the same as those in Example 4.

Example 20

While nitrogen was injected (2 L/min) at a reduced pressure of 666 Pa, 1 kg of the ethyl-2-cyanoacrylate adhesive composition obtained in Synthesis Example 2 was deaerated for 24 hours at a temperature of 30° C. Then, to this ethyl-2-cyanoacrylate adhesive composition obtained as a result of deaeration, a $BF_3$ diethyl ether complex was added and an ethyl-2-cyanoacrylate adhesive composition was prepared so that a content of the $BF_3$ diethyl ether complex was 15 ppm. Further, to thus prepared ethyl-2-cyanoacrylate adhesive composition, 15-crown-5-ether and trimellitic acid were added and mixed so that a content of 15-crown-5-ether was 800 ppm and a content of trimellitic acid was 400 ppm. Subsequently, a sample of thus obtained ethyl-2-cyanoacrylate adhesive composition was collected and subjected to a whitening test, an order sensing test, and measurement of an ethanol content and an acrylonitrile content. Table 4 shows a result of Example 20.

Example 21

To an ethyl-2-cyanoacrylate adhesive composition that was obtained under the same condition as in Example 7 other than a condition such that, after deaeration, a content of $SO_2$ was arranged to be 40 ppm, hydrophobic silica was added and mixed. A content of the hydrophobic silica was set to be 5% by weight with respect to a total weight of the ethyl-2-cyanoacrylate adhesive composition prepared by adding $SO_2$ as described above. The hydrophobic silica here has pH in a range of 5 to 6 in a case where the hydrophobic silica is dispersed at 4% by weight in a solution having a proportion of

TABLE 3

|  | EXAMPLES |  |  |  |  |  | COMPARATIVE EXAMPLE |
|---|---|---|---|---|---|---|---|
|  | 14 | 15 | 16 | 17 | 18 | 19 | 4 |
| ETHANOL CONTENT (ppm) | 50 | 40 | 57 | 50 | 60 | 90 | 180 |
| ACRYLONITRILE CONTENT (ppm) | 25 | 20 | 29 | 25 | 30 | 20 | 100 |
| SUM TOTAL (ppm) OF ETHANOL CONTENT AND ACRYLONITRILE CONTENT | 75 | 60 | 86 | 75 | 90 | 110 | 280 |
| $SO_2$ (ppm) | 17 | 14 | 19 | 17 | 20 |  |  |
| $HBF_4$ (ppm) |  |  |  |  |  | 10 | 10 |
| CROWN ETHER (ppm) |  |  |  |  |  |  |  |
| CALIXARENE (ppm) |  |  |  |  |  |  |  |
| DIMETHYL PHTHALATE (% BY WEIGHT) | 20 | 45 |  |  |  |  |  |
| HYDROPHOBIC SILICA (% BY WEIGHT) |  |  | 5 | 20 |  |  |  |
| TRIMELLITIC ACID (ppm) |  |  |  |  |  |  | 400 |
| SALICYLIC ACID (ppm) |  |  |  |  | 400 | 1000 |  |
| GALLIC ACID (ppm) |  |  |  |  |  |  |  |
| PYROGALLOL (ppm) |  |  |  |  |  |  |  |
| ODOR SENSING TEST | GOOD | GOOD | GOOD | FAIR | GOOD | FAIR | POOR |
| WHITENING TEST (RUBBER) | GOOD | FAIR | GOOD | FAIR | GOOD | FAIR | POOR |
| WHITENING TEST (PLATING) | FAIR | FAIR | FAIR | FAIR | GOOD | GOOD | POOR |
| WHITENING TEST (ACRYLIC RESIN) | FAIR | FAIR | FAIR | FAIR | FAIR | GOOD/FAIR | POOR | water/methanol=1:1 (wt/wt). In addition, gallic acid was added and mixed so that a content of the gallic acid was 500 ppm. Then, a sample of thus obtained ethyl-2-cyanoacrylate adhesive composition was collected and subjected to a whitening test, an order sensing test, and measurement of an ethanol content and an acrylonitrile content. Table 4 shows a result of Example 21.

Example 22

To an ethyl-2-cyanoacrylate adhesive composition that was obtained in Example 1 and that had been deaerated, 15-crown-5-ether and pyrogallol were added and mixed so that a content of 15-crown-5-ether was 1000 ppm and a content of pyrogallol was 500 ppm. Then, a sample of thus obtained ethyl-2-cyanoacrylate adhesive composition was collected and subjected to a whitening test and an order sensing test. Table 4 shows a result of Example 22. An ethanol content and an acrylonitrile content are the same as those in Example 1.

Example 23

To an ethyl-2-cyanoacrylate adhesive composition that was obtained under the same condition as in Example 7 other than a condition such that, after deaeration, a content of $SO_2$ was arranged to be 80 ppm, 5,11,17,23-tetratertiarybutyl-25,26,27,28-tetra(2-ethoxy-2-oxoethoxy)calix(4)arene and pyrogallol were added and mixed. Here, a content of 5,11,17,23-tetratertiarybutyl-25,26,27,28-tetra(2-ethoxy-2-oxoethoxy)calix(4)arene was arranged to be 4000 ppm and a content of pyrogallol was arranged to be 5000 ppm. Then, a sample of thus obtained ethyl-2-cyanoacrylate adhesive composition was collected and subjected to a whitening test and an order sensing test. Table 4 shows a result of Example 23. An ethanol content and an acrylonitrile content are the same as those in Example 7.

Example 24

While nitrogen was injected (2 L/min) at a reduced pressure of 666 Pa, 1 kg of the ethyl-2-cyanoacrylate adhesive composition obtained in Synthesis Example 2 was deaerated for 4 hours at a temperature of 30° C. Then, $SO_2$ was added so that a content of $SO_2$ was 20 ppm. To thus prepared ethyl-2-cyanoacrylate adhesive composition, $HBF_4$, 18-crown-6-ether, and trimellitic acid were added and mixed so that: a content of $HBF_4$ was 2 ppm; a content of 18-crown-6-ether was 100 ppm; and a content of trimellitic acid was 100 ppm. Subsequently, a sample of this ethyl-2-cyanoacrylate adhesive composition was collected and subjected to a whitening test, an order sensing test, and measurement of an ethanol content and an acrylonitrile content. Table 4 shows a result of Example 24.

TABLE 4

| | EXAMPLES | | | | |
|---|---|---|---|---|---|
| | 20 | 21 | 22 | 23 | 24 |
| ETHANOL CONTENT (ppm) | 20 | 57 | 20 | 60 | 90 |
| ACRYLONITRILE CONTENT (ppm) | 10 | 29 | 10 | 30 | 20 |
| SUM TOTAL (ppm) OF ETHANOL CONTENT AND ACRYLONITRILE CONTENT | 30 | 86 | 30 | 90 | 110 |
| $SO_2$ (ppm) | | 38 | | 80 | 20 |
| $HBF_4$ (ppm) | | | 10 | | 2 |
| $BF_3$ DIETHYL ETHER COMPLEX (ppm) | 15 | | | | |
| CROWN ETHER (ppm) | 800 | | 1000 | | 100 |
| CALIXARENE (ppm) | | | | 4000 | |
| DIMETHYL PHTHALATE (% BY WEIGHT) | | | | | |
| HYDROPHOBIC SILICA (% BY WEIGHT) | | | 5 | | |
| TRIMELLITIC ACID (ppm) | 400 | | | | 100 |
| SALICYLIC ACID (ppm) | | | | | |
| GALLIC ACID (ppm) | | 500 | | | |
| PYROGALLOL (ppm) | | | 500 | 5000 | |
| ODOR SENSING TEST | GOOD | GOOD | GOOD | GOOD | FAIR |
| WHITENING TEST (RUBBER) | GOOD | GOOD | GOOD | GOOD | GOOD |
| WHITENING TEST (PLATING) | GOOD | GOOD/FAIR | GOOD | GOOD/FAIR | GOOD/FAIR |
| WHITENING TEST (ACRYLIC RESIN) | GOOD | GOOD/FAIR | GOOD | GOOD/FAIR | GOOD/FAIR |

Comparative Example 1

The ethyl-2-cyanoacrylate adhesive composition obtained in Synthesis Example 1 was subjected to a whitening test, an order sensing test, and measurement of an ethanol content and an acrylonitrile content. Table 1 shows a result of Comparative Example 1.

Comparative Example 2

To the ethyl-2-cyanoacrylate adhesive composition deaerated as in Example 1, ethanol and acrylonitrile were added so that an ethanol content was 300 ppm and an acrylonitrile content was 200 ppm. Then, thus obtained ethyl-2-cyanoacrylate adhesive composition was subjected to a whitening test, an order sensing test, and measurement of an ethanol content and an acrylonitrile content. Table 1 shows a result of Comparative Example 2.

Comparative Example 3

To the ethyl-2-cyanoacrylate adhesive composition that was prepared in Example 8 so that the content of $SO_2$ was 40 ppm, acrylonitrile and 5,11,17,23-tetratertiarybutyl-25,26,27,28-tetra(2-ethoxy-2-oxoethoxy)calix(4)arene were added so that an acrylonitrile content was 120 ppm and a content of 5,11,17,23-tetratertiarybutyl-25,26,27,28-tetra(2-ethoxy-2-oxoethoxy)calix(4)arene was 1000 ppm. Then, thus obtained ethyl-2-cyanoacrylate adhesive composition was subjected to a whitening test, an order sensing test, and measurement of an ethanol content and an acrylonitrile content. Table 2 shows a result of Comparative Example 3.

Comparative Example 4

To the ethyl-2-cyanoacrylate adhesive composition in Comparative Example 1, trimellitic acid was added so that a content of trimellitic acid was 400 ppm. Then, thus obtained ethyl-2-cyanoacrylate adhesive composition was subjected to a whitening test and an order sensing test. Table 3 shows a result of Comparative Example 4. An ethanol content and an acrylonitrile content are the same as those in Comparative Example 1.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

According to a method for producing an ethyl-2-cyanoacrylate adhesive composition by purification and the ethyl-2-cyanoacrylate adhesive composition according to the present invention, it is possible to significantly improve conventional problems of ethyl-2-cyanoacrylate adhesive compositions, that is, irritating odor and whitening, as compared to conventional ethyl-2-cyanoacrylate adhesive compositions. Therefore, the present invention is applicable and very useful in a wide range, not only in adhesive manufacturing industries but also in various industries such as an electronics industry, an electric industry, and automotive industry.

The invention claimed is:

1. A method for purifying an ethyl-2-cyanoacrylate adhesive composition, the method comprising carrying out deaeration of the ethyl-2-cyanoacrylate adhesive composition at the same time as injection of an inactive gas at a reduced pressure in a range of 100 Pa to 10000 Pa at a temperature in a range of 5° C. to 50° C. so that the ethyl-2-cyanoacrylate adhesive composition has a sum total of an acrylonitrile content and an ethanol content in a range of 1 ppm to 150 ppm.

2. An ethyl-2-cyanoacrylate adhesive composition having a sum total of an acrylonitrile content and an ethanol content in a range of 1 ppm to 150 ppm.

3. The ethyl-2-cyanoacrylate adhesive composition as set forth in claim 2, wherein the acrylonitrile content is 50 ppm or less.

4. The ethyl-2-cyanoacrylate adhesive composition as set forth in claim 2, wherein:
the ethanol content is 100 ppm or less; and
the acrylonitrile content is 50 ppm or less.

5. The ethyl-2-cyanoacrylate adhesive composition as set forth in claim 2, further comprising $SO_2$,
wherein a content of the $SO_2$ is in a range of 30 ppm to 100 ppm.

6. The ethyl-2-cyanoacrylate adhesive composition as set forth in claim 2, further comprising $HBF_4$ and/or $BF_3$ ether complex,
wherein a total content of the $HBF_4$ and/or the $BF_3$ ether complex is in a range of 1 ppm to less than 20 ppm.

7. The ethyl-2-cyanoacrylate adhesive composition as set forth in claim 2, further comprising at least one compound selected from a group consisting of crown ethers and calixarene derivatives,
wherein a total content of the at least one compound is in a range of 50 ppm to 5000 ppm.

8. The ethyl-2-cyanoacrylate adhesive composition as set forth in claim 2, further comprising at least one compound selected from a group consisting of phthalate esters and acetyl citrate esters,
wherein a total content of the at least one compound is in a range of 5% by weight to 40% by weight.

9. The ethyl-2-cyanoacrylate adhesive composition as set forth in claim 2, further comprising at least one compound represented by a general formula (1):

[Chem. 1]

wherein: R represents one or a combination of two or more kinds of a carboxyl group, a carboxylic anhydride, an aldehyde group, a hydroxyl group, an alkoxy group and a carboxylic acid ester group excluding polycarboxylic acid ester; and n is an integer in a range of 2 to 6,
wherein a total content of the at least one compound is in a range of 10 ppm to 5000 ppm.

10. The ethyl-2-cyanoacrylate adhesive composition as set forth in claim 2, further comprising hydrophobic silica in a range of 1% by weight to 15% by weight, the hydrophobic silica having a property such that the hydrophobic silica has pH in a range of 4 to 7 in a case where the hydrophobic silica is dispersed at 4% by weight in a solution having a proportion of water/methanol=1:1 (wt/wt).

11. The ethyl-2-cyanoacrylate adhesive composition as set forth in claim 7, further comprising $SO_2$,
wherein a content of the $SO_2$ is in a range of 30 ppm to 100 ppm.

12. The ethyl-2-cyanoacrylate adhesive composition as set forth in claim 7, further comprising $HBF_4$ and/or $BF_3$ ether complex,
wherein a total content of the $HBF_4$ and/or the $BF_3$ ether complex is in a range of 1 ppm to 10 ppm.

13. The ethyl-2-cyanoacrylate adhesive composition as set forth in claim 7, wherein the sum total of the acrylonitrile content and the ethanol content is in a range of 1 ppm to 100 ppm.

14. The ethyl-2-cyanoacrylate adhesive composition as set forth in claim 8, further comprising $SO_2$,
wherein a content of the $SO_2$ is in a range of 30 ppm to 100 ppm.

15. The ethyl-2-cyanoacrylate adhesive composition as set forth in claim 9, further comprising $SO_2$,
wherein a content of the $SO_2$ is in a range of 30 ppm to 100 ppm.

16. The ethyl-2-cyanoacrylate adhesive composition as set forth in claim 9, further comprising $HBF_4$ and/or $BF_3$ ether complex,
wherein a total content of the $HBF_4$ and/or the $BF_3$ ether complex is in a range of 1 ppm to 10 ppm.

17. The ethyl-2-cyanoacrylate adhesive composition as set forth in claim 10, further comprising $SO_2$,
wherein a content of the $SO_2$ is in a range of 30 ppm to 100 ppm.

* * * * *